United States Patent
Bingham

(10) Patent No.: US 10,444,195 B2
(45) Date of Patent: Oct. 15, 2019

(54) DETECTION OF NEAR SURFACE INCONSISTENCIES IN STRUCTURES

(71) Applicant: The Boeing Company, Chicago, IL (US)

(72) Inventor: Jill Paisley Bingham, Seattle, WA (US)

(73) Assignee: The Boeing Company, Chicago, IL (US)

(*) Notice: Subject to any disclaimer, the term of this patent is extended or adjusted under 35 U.S.C. 154(b) by 523 days.

(21) Appl. No.: 15/147,426

(22) Filed: May 5, 2016

(65) Prior Publication Data
US 2017/0322184 A1 Nov. 9, 2017

(51) Int. Cl.
*G01N 29/04* (2006.01)
*G01N 29/46* (2006.01)
*G01N 29/24* (2006.01)
*G01N 29/42* (2006.01)
*G01B 17/02* (2006.01)

(52) U.S. Cl.
CPC ......... *G01N 29/043* (2013.01); *G01B 17/025* (2013.01); *G01N 29/2418* (2013.01); *G01N 29/42* (2013.01); *G01N 29/46* (2013.01); *G01N 2291/0289* (2013.01); *G01N 2291/02854* (2013.01)

(58) Field of Classification Search
CPC .. G01N 29/043; G01N 29/2418; G01N 29/46; G01N 29/42; G01N 2291/02854; G01N 2291/0289; G01B 17/025
See application file for complete search history.

(56) References Cited

U.S. PATENT DOCUMENTS

| | | | |
|---|---|---|---|
| 9,164,066 B1 | 10/2015 | Bossi et al. | |
| 9,188,566 B2 | 11/2015 | Georgeson et al. | |
| 9,250,213 B1 | 2/2016 | Bossi et al. | |
| 2002/0152813 A1* | 10/2002 | Dixon | G01B 11/0666 73/579 |
| 2003/0054182 A1* | 3/2003 | Keener | B05D 3/0254 428/457 |
| 2009/0025479 A1* | 1/2009 | Kollgaard | G01N 29/04 73/599 |
| 2012/0253180 A1* | 10/2012 | Emelianov | A61B 8/0841 600/424 |
| 2014/0116146 A1 | 5/2014 | Bossi et al. | |

OTHER PUBLICATIONS

Tang ("A resonance-type ultrasonic thickness gage for measuring the wall thickness and corrosion of chemical plant equipment", 1968, see attached publication).*
Bossi et al., "Ultrasound Inspection System for Inspecting a Test Object with Non-Planar Features," U.S. Appl. No. 13/526,853, filed Jun. 19, 2012, 62 pages.

* cited by examiner

*Primary Examiner* — Xin Y Zhong
(74) *Attorney, Agent, or Firm* — Yee & Associates, P.C.

(57) ABSTRACT

A method of detecting near surface inconsistencies in a structure is presented. A pulsed laser beam is directed towards the structure. Wide-band ultrasonic signals are formed in the structure when radiation of the pulsed laser beam is absorbed by the structure. The wide-band ultrasonic signals are detected to form data. The data is processed to identify a frequency associated with the near surface inconsistency.

20 Claims, 9 Drawing Sheets

DETECTION OF NEAR SURFACE INCONSISTENCIES IN STRUCTURES

BACKGROUND INFORMATION

1. Field

The present disclosure relates generally to non-destructive inspection and, in particular, to performing non-destructive inspection on a structure. Still more particularly, the present disclosure relates to a method and apparatus for detecting near surface inconsistencies in a structure.

2. Background

In manufacturing aircraft, vehicles, and other structures, inspection of parts used to form these structures is often performed to determine whether the parts will have desired parameters for a desired performance of the part. Additionally, the structures and parts are inspected as part of normal maintenance when the aircraft, vehicles, and other structures are in use.

Non-destructive testing is commonly performed on these parts. Non-destructive testing is used to evaluate the properties of a part without altering the ability to use the part in service.

Ultrasound testing is a type of non-destructive testing. Ultrasound testing is often used to perform inspections on aircraft parts that include, or are comprised of, composite materials. Ultrasound testing involves transmitting acoustic waves through a test object, such as an aircraft part or structure.

However, near surface inconsistencies may not be detectable using conventional ultrasound techniques. Therefore, it would be desirable to have a method and apparatus that take into account at least some of the issues discussed above, as well as other possible issues.

SUMMARY

In one illustrative embodiment, a method of detecting a presence of a near surface inconsistency in a structure is presented. A pulsed laser beam is directed towards the structure. Wide-band ultrasonic signals are formed in the structure when radiation of the pulsed laser beam is absorbed by the structure. The wide-band ultrasonic signals are detected to form data. The data is processed to identify a frequency associated with the near surface inconsistency, wherein the frequency is indicative of the presence of the near surface inconsistency.

In another illustrative embodiment, a method of detecting a presence of a near surface inconsistency in a composite structure is presented. A pulsed laser beam is directed towards the composite structure. Wide-band ultrasonic signals are formed in the composite structure when radiation of the pulsed laser beam is absorbed by the composite structure. The wide-band ultrasonic signals are detected to form data. The data is filtered based on a desired depth of detection. A frequency associated with the near surface inconsistency is determined, wherein the frequency is indicative of the presence of the near surface inconsistency.

In a further illustrative embodiment, a method of measuring thickness of an organic coating on a surface of a substrate is presented. A pulsed laser beam is directed towards the organic coating. Wide-band ultrasonic signals are formed in the organic coating and the substrate when radiation of the pulsed laser beam is absorbed by the organic coating and the substrate. The wide-band ultrasonic signals are detected to form data. The data is filtered based on a desired depth of detection. A frequency associated with the thickness of the organic coating is determined. The thickness of the organic coating is determined based on the frequency.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account one or more different considerations. For example, the illustrative embodiments recognize and take into account that conventional ultrasound systems use lower frequency transducers. For example, conventional ultrasound systems use piezoelectric transducers with have a narrow band. Aerospace composite inspection systems typically use lower center frequencies of 3.5-5 MHz. Very near surface defects appear as a change in the front surface echo using conventional ultrasound systems. This change in the front surface echo is undesirably difficult to recognize.

The different illustrative embodiments recognize and take into account that laser ultrasound inspection systems are currently being used. The different illustrative embodiments recognize and take into account that laser ultrasound is unique compared to conventional ultrasound due to the wideband generation and reception of ultrasound in the part. However, the different illustrative embodiments further recognize and take into account that currently no processes exist for identifying very near surface defects using laser ultrasound inspection systems.

Figure 1:
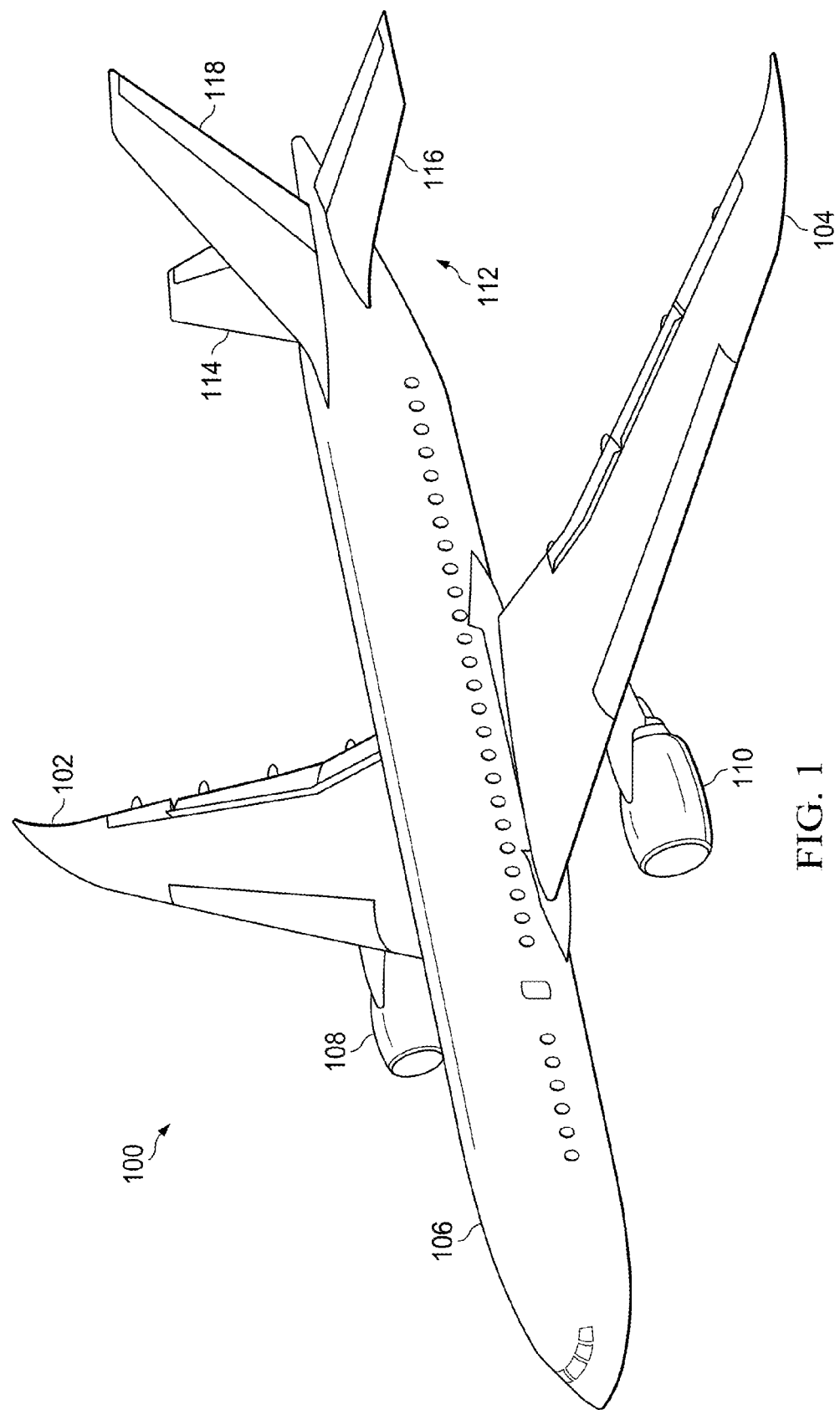
FIG. 1 is an illustration of an aircraft in which an illustrative embodiment may be implemented.

With reference now to the figures, and in particular, with reference to FIG. 1, an illustration of an aircraft is depicted in which an illustrative embodiment may be implemented. In this illustrative example, aircraft 100 has wing 102 and wing 104 attached to body 106. Aircraft 100 includes engine 108 attached to wing 102 and engine 110 attached to wing 104.

Body 106 has tail section 112. Horizontal stabilizer 114, horizontal stabilizer 116, and vertical stabilizer 118 are attached to tail section 112 of body 106. Aircraft 100 is an example of an aircraft having composite structures or structures formed of other materials that may be inspected with a laser ultrasound inspection system in accordance with an illustrative embodiment. For example, at least one of wing 102 or wing 104 may be inspected for near surface inconsistencies using a laser ultrasound inspection system.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, thing, or a category.

For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations.

This illustration of aircraft 100 is provided for purposes of illustrating one environment in which the different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, a rotorcraft, or other suitable types of aircraft.

Although the illustrative examples for an illustrative embodiment are described with respect to an aircraft, an illustrative embodiment may be applied to other types of platforms. The platform may be, for example, a mobile platform, a stationary platform, a land-based structure, an aquatic-based structure, or a space-based structure. More specifically, the platform may be a surface ship, a tank, a personnel carrier, a train, a spacecraft, a space station, a satellite, a submarine, an automobile, a manufacturing facility, a building, or other suitable platforms.

Further, although the structures may be formed of composite materials, a multi-modal inspection may be performed for any desirable type of material. For example, a plurality of waves may be used to inspect ceramics or metals.

Figure 2:
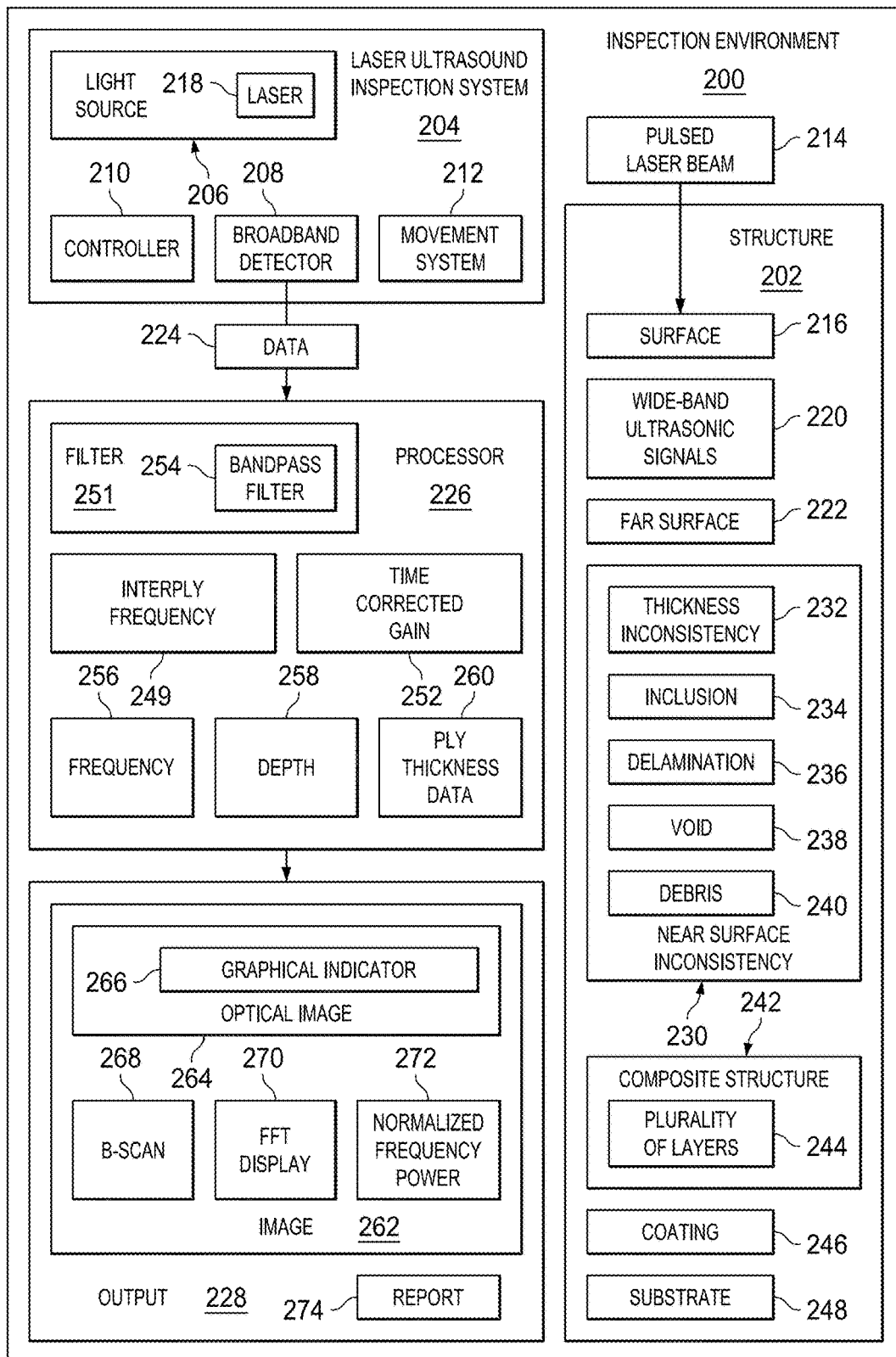
FIG. 2 is an illustration of a block diagram of an inspection environment in accordance with an illustrative embodiment.

With reference now to FIG. 2, an illustration of a block diagram of an inspection environment is depicted in accordance with an illustrative embodiment. As depicted, inspection environment 200 includes structure 202. Structure 202 may take any number of forms. For example, structure 202 may be a part for an aircraft.

Structure 202 may be inspected using laser ultrasound inspection system 204. As depicted, laser ultrasound inspection system 204 includes light source 206, broadband detector 208, controller 210, and movement system 212.

In these illustrative examples, controller 210 controls the operation of laser ultrasound inspection system 204. Controller 210 may be implemented using hardware, software, firmware, or a combination thereof.

In some illustrative examples, controller 210 may be implemented within a computer system. The computer system may be one or more computers. When more than one computer is present in the computer system, those computers may be in communication with each other through a communications medium such as a network.

When software is used, the operations performed by controller 210 may be implemented using, for example, without limitation, program code configured to run on a processor unit. When firmware is used, the operations performed by controller 210 may be implemented using, for example, without limitation, program code and data stored in persistent memory to run on a processor unit.

When hardware is employed, the hardware may include one or more circuits that operate to perform the operations performed by controller 210. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In some illustrative examples, the operations and/or processes performed by controller 210 may be performed using organic components integrated with inorganic components. In some cases, the operations and/or processes may be performed by entirely organic components, excluding a human being. As one illustrative example, circuits in organic semiconductors may be used to perform these operations and/or processes.

Movement system 212 is configured to move light source 206 and broadband detector 208 relative to structure 202. Movement system 212 may be implemented using a number of different types of systems. For example, movement system 212 may be a robot. The robot may be, for example, a robotic arm that may move broadband detector 208 about a number of axes. Movement system 212 also may be, for example, without limitation, a gantry robot, a hand-operated scanning head, and other suitable types of movement systems.

Light source 206 is configured to transmit pulsed laser beam 214 onto surface 216 of structure 202. In some illustrative examples, light source 206 is laser 218. More specifically, laser 218 may be a diode-pumped nanosecond laser.

Pulsed laser beam 214 is configured to form wide-band ultrasonic signals 220 within structure 202 when pulsed laser beam 214 encounters structure 202. For example, energy in pulsed laser beam 214 may cause thermoelastic expansion in structure 202. The thermoelastic expansion may result in wide-band ultrasonic signals 220 in structure 202. Wide-band ultrasonic signals 220 may have, for example, a frequency from about 20 kilohertz to about 100 megahertz depending on the particular implementation. The frequency for wide-band ultrasonic signals 220 may depend on the material used to form structure 202, the pulse width of the laser excitation, and other suitable factors. Wide-band ultrasonic signals 220 travel from surface 216 towards far surface 222.

Broadband detector 208 is configured to detect wide-band ultrasonic signals 220 that may occur as a result of scattering, reflection, modulation, and other changes to acoustic waves traveling within structure 202. In one example, broadband detector 208 may comprise any form of interferometer. For example, broadband detector 208 may include a fiber-optic modified Sagnac interferometer for non-contact detection of backscattered ultrasound.

Broadband detector 208 sends data 224 to processor 226. Data 224 is used by processor 226 to generate output 228. Data 224 may include a full-bandwidth signal for a location of structure 202 being inspected. As laser ultrasound inspection system 204 is scanned across structure 202, data 224 for a plurality of locations on structure 202 is collected.

As depicted, output 228 may indicate whether near surface inconsistency 230 is present in structure 202. Near surface inconsistency 230 may be, for example, without limitation, thickness inconsistency 232, inclusion 234, delamination 236, void 238, or debris 240. Near surface inconsistency 230 is within 0.25 inches of surface 216. In some examples, near surface inconsistency 230 is within 0.10 inches of surface 216. In some examples, near surface inconsistency 230 is within 0.005 inches of surface 216.

Structure 202 may be at least one of composite structure 242 formed of plurality of layers 244 or coating 246 on substrate 248. Plurality of layers 244 may also be referred to as a plurality of plies. When structure 202 is composite structure, near surface inconsistency 230 may be one of inclusion 234, delamination 236, void 238, or debris 240. When structure 202 is coating 246 on substrate 248, near surface inconsistency 230 is thickness inconsistency 232.

Coating 246 is any desirable organic material. Coating 246 may also be referred to as a surface coating, an organic coating or a surface organic coating. In one example, substrate 248 may be one of composite material or a metal. When substrate 248 is a composite material, coating 246 has a different thickness*sound velocity product than the periodicity of the composite material. In some examples, a different thickness sound velocity product than the composite material is accomplished by coating 246 being thicker than the periodicity of the composite material.

When interrogating a layered material, such as a composite material, the periodic layering causes a unique frequency signature of structure 202. The frequency signature of the composite material is interply frequency 249. Interply frequency 249 is affected by the thickness of the material and the sound speed travelling through it. Interply frequency 249 is calculated using the equation $1/(t*2/s)=i$, wherein t is the thickness per ply of the composite material, wherein s is the speed of sound through structure 202, and wherein i is interply frequency 249. Taking a Fast Fourier Transform (FFT) of wide-band ultrasonic signals 220 shows the interply frequency 249.

When structure 202 is composite structure 242, near surface inconsistency 230 may be referred to as being within a number of layers from surface 216 in plurality of layers 244. In some examples, near surface inconsistency 230 is within three plies of surface 216. The thickness of a ply of composite structure 242 is any desirable thickness. The thickness of a ply is determined by the material of the ply as well as other design considerations of composite structure 242. In some illustrative examples, a ply is in the range of 0.005" to 0.05" thick.

In some examples, processor 226 applies at least one of filter 251 or time corrected gain 252 to data 224. In some examples, filter 251 takes the form of bandpass filter 254. Bandpass filter 254 is selected based on physical parameters structure 202 and a type of inconsistency to detect. Bandpass filter 254 may have any desirable range. In some illustrative examples, when structure 202 includes a composite material, bandpass filter 254 is selected based on interply frequency 249 of the composite material. For example, when structure 202 includes a composite material, bandpass filter 254 is selected to exclude interply frequency 249. In some illustrative examples, bandpass filter 254 is a bandpass 2-10 MHz filter. In other illustrative examples, bandpass filter 254 is a bandpass 2-7 MHz filter.

In some illustrative examples, data 224 comprises a number of ultrasonic A-scans in the time domain. In these illustrative examples, processing data 224 comprises transforming the number of ultrasonic A-scans to generate frequency domain data. Applying filter 251 is performed on the frequency domain data. When time corrected gain 252 is performed, time corrected gain 252 is applied to the number of ultrasonic A-scans in the time domain.

Processor 226 processes data 224 to identify frequency 256 associated with near surface inconsistency 230. As frequency 256 is associated with near surface inconsistency 230, frequency 256 is not present when near surface inconsistency 230 is absent. Accordingly, frequency 256 is indicative of the presence of near surface inconsistency 230 within structure 202. Further, frequency 256 is used to identify characteristics of near surface inconsistency 230, such as a location or thickness of near surface inconsistency 230.

When looking for near surface inconsistency 230, near surface inconsistency 230 causes "ringing" in the wide-band ultrasonic signals 220. The "ringing" causes frequency 256 to be different from interply frequency 249. Using frequency 256, characteristics of near surface inconsistency 230 are determined.

When structure 202 is composite structure 242, processor 226 also determines depth 258 of near surface inconsistency 230 using frequency 256. In some illustrative examples, processor 226 determines depth 258 using the equation $(1/f)*s/2=d$, wherein f is frequency 256, wherein s is the speed of sound through structure 202, and wherein d is depth 258 of near surface inconsistency 230.

When structure 202 is composite structure 242, processor 226 determines a location of near surface inconsistency 230 based on depth 258 and ply thickness data 260 of structure 202. For example, processor 226 may determine that near surface inconsistency 230 is present between the first and second plies of plurality of layers 244. As another example, processor 226 may determine that near surface inconsistency 230 is present in the second ply of plurality of layers 244.

When structure 202 is substrate 248 having coating 246, processor 226 determines a thickness of near surface inconsistency 230 using frequency 256. In some illustrative examples, processor 226 determines a thickness of near surface inconsistency 230 using the equation $(1/f)*s/2=d$, wherein f is frequency 256, wherein s is the speed of sound through coating 246, and wherein d is the thickness of near surface inconsistency 230.

Output 228 takes any desirable form. In one illustrative example, output 228 is image 262. Image 262 may be displayed on any desirable display device. In some examples, image 262 is optical image 264. Optical image 264 is an image of a portion or all of surface 216 of structure 202. In some examples, optical image 264 includes graphical indicator 266. Optical image 264 is displayed with graphical indicator 266 when near surface inconsistency 230 is present in structure 202. Graphical indicator 266 is displayed in a location in optical image 264 corresponding to a location in structure 202 where near surface inconsistency 230 is detected. In other illustrative examples, if near surface inconsistency 230 is absent, graphical indicator 266 may be displayed to indicate an absence of near surface inconsistency 230.

In other illustrative examples, image 262 is at least one of B-scan 268, FFT display 270, or normalized frequency power 272. B-scan 268 displays any desirable data. In some illustrative examples, B-scan 268 is a display of wide-band ultrasonic signals 220 after processing. FFT display 270 is a display of wide-band ultrasonic signals 220 after undergoing a Fast Fourier Transform.

As still another illustrative example, output 228 may take the form of report 274. Report 274 may identify near surface inconsistency 230 in structure 202. Report 274 also may include other information, such as locations of inconsistencies, types of inconsistencies, sizes of inconsistencies, and other suitable types of information. In some examples, report 274 provides one of the depth or thickness of near surface inconsistency 230.

The illustration of inspection environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, inspection environment 200 may include a display for displaying output 228. This display may take any desirable form. For example, the display may be a computer screen, a tablet, a phone, a projector, a wearable display, or any other type of desirable display.

As another example, inspection environment 200 may include another inspection system other than laser ultrasound inspection system 204. For example, inspection equipment 200 may include some other form of conventional ultrasonic inspection equipment.

Figure 3:
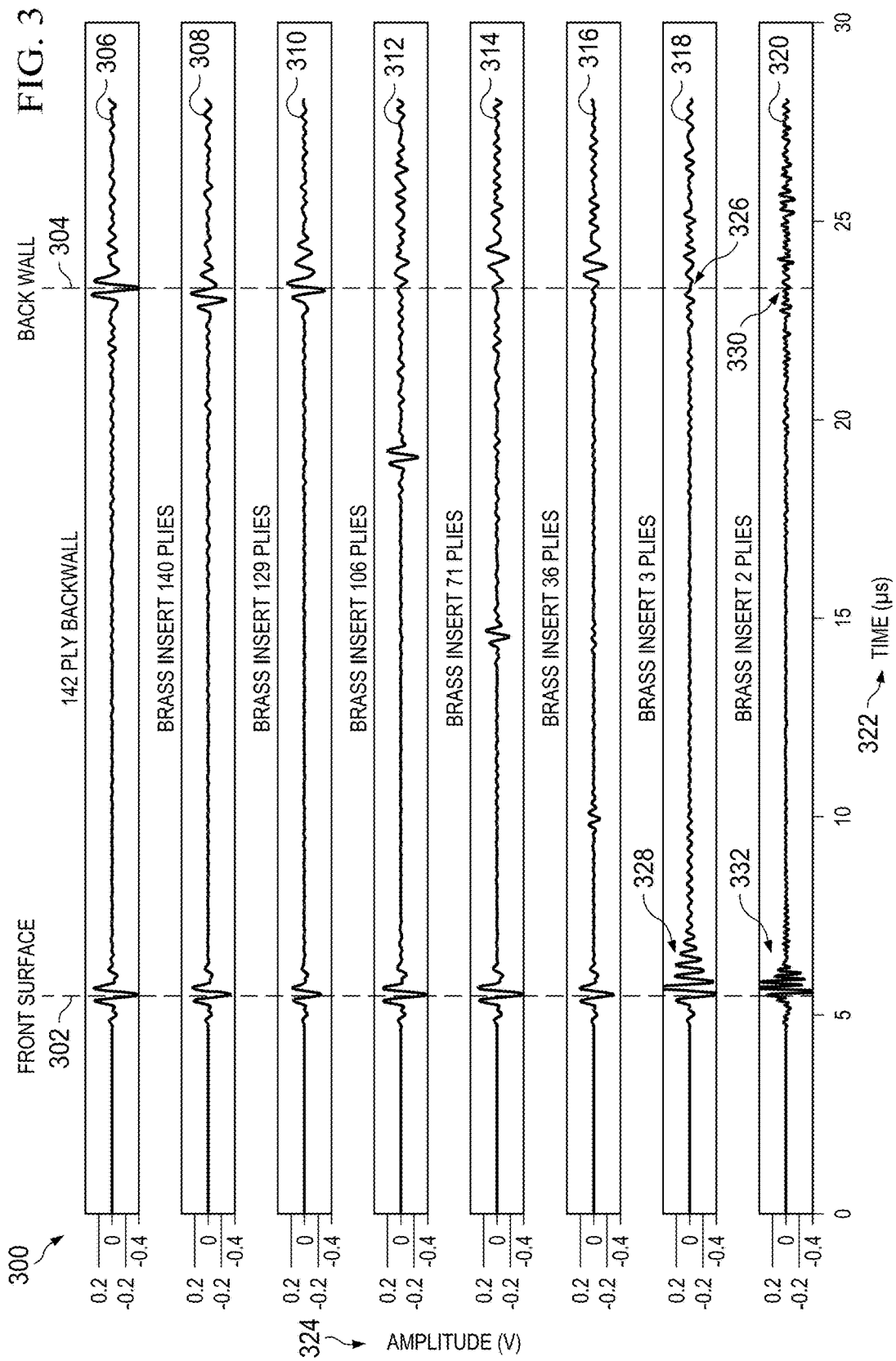
FIG. 3 is an illustration of a plurality of A-scans in accordance with an illustrative embodiment.

Turning now to FIG. 3, an illustration of a plurality of A-scans is depicted in accordance with an illustrative embodiment. Plurality of A-scans 300 is an implementation of output 228 of FIG. 2 after inspecting structure 202. Plurality of A-scans 300 is an example of inspection output for a composite structure, such as a portion of aircraft 100 of FIG. 1.

Plurality of A-scans 300 represents wide-band ultrasonic signals of a plurality of locations of a composite structure. In some illustrative examples, the composite structure is a test structure formed to demonstrate data from an inspection. In this example, each location has the same quantity of composite layers. In fact, in this example, each location has the same composite layers. For example, each of plurality of A-scans 300 has peak 302 representing the front surface of the composite structure and peak 304 representing the far surface of the composite structure.

A test structure has representative inconsistencies at known locations to demonstrate capabilities of an inspection method. In this fashion, it is determined if an inspection method detects each of the known representative inconsistencies. In this illustrative example, brass inserts are included at designated locations of a test structure.

In this illustrative example, plurality of A-scans 300 has received processing. For example, the received wide-band ultrasonic signals have received at least one of filtering or time corrected gain.

Plurality of A-scans 300 includes B-scan 306, A-scan 308, A-scan 310, A-scan 312, A-scan 314, A-scan 316, A-scan 318, and A-scan 320. Each of plurality of A-scans 300 has x-axis 322 and y-axis 324. X-axis 322 is the received time for the wide-band ultrasound signals. Y-axis 324 is the amplitude of wide-band ultrasound signals.

A-scan 306 is the output from a first location of the composite structure. The first location of the composite structure has 142 composite plies. The first location of the composite structure does not have any inconsistencies.

A-scan 308 is the output from a second location of the composite structure. The second location of the composite structure has 142 composite plies. The second location of the composite structure has an inconsistency near the far surface. In this illustrative example, a brass insert has been placed after 140 plies.

A-scan 310 is the output from a third location of the composite structure. The third location of the composite structure has 142 composite plies. The third location of the composite structure has an inconsistency. In this illustrative example, a brass insert has been placed after 139 plies.

A-scan 312 is the output from a fourth location of the composite structure. The fourth location of the composite structure has 142 composite plies. The fourth location of the composite structure has an inconsistency. In this illustrative example, a brass insert has been placed after 106 plies.

A-scan 314 is the output from a fifth location of the composite structure. The fifth location of the composite structure has 142 composite plies. The fifth location of the composite structure has an inconsistency. In this illustrative example, a brass insert has been placed after 71 plies.

A-scan 316 is the output from a sixth location of the composite structure. The sixth location of the composite structure has 142 composite plies. The sixth location of the composite structure has an inconsistency. In this illustrative example, a brass insert has been placed after 36 plies.

A-scan 318 is the output from a seventh location of the composite structure. The seventh location of the composite structure has 142 composite plies. The seventh location of the composite structure has a near surface inconsistency. In this illustrative example, a brass insert has been placed after 3 plies.

A-scan 318 does not contain peak 304 representing the far surface of the composite structure at location 326. Not having peak 304 is an indication of an inconsistency. Further, A-scan 318 has ringing 328 near peak 302 representing the surface of the composite structure.

A-scan 320 is the output from an eighth location of the composite structure. The eighth location of the composite structure has 142 composite plies. The eighth location of the composite structure has a near surface inconsistency. In this illustrative example, a brass insert has been placed after 2 plies.

A-scan 320 does not contain peak 304 representing the far surface of the composite structure at location 330. Not having peak 304 is an indication of an inconsistency. Further, A-scan 320 has ringing 332 near peak 302 representing the surface of the composite structure.

However, based on a Fast Fourier Transform of the data for plurality of A-scans 300, near surface inconsistencies are identified. Further, the depth or thickness of the near surface inconsistencies is determined based on a speed of sound through the composite structure.

Figure 4:
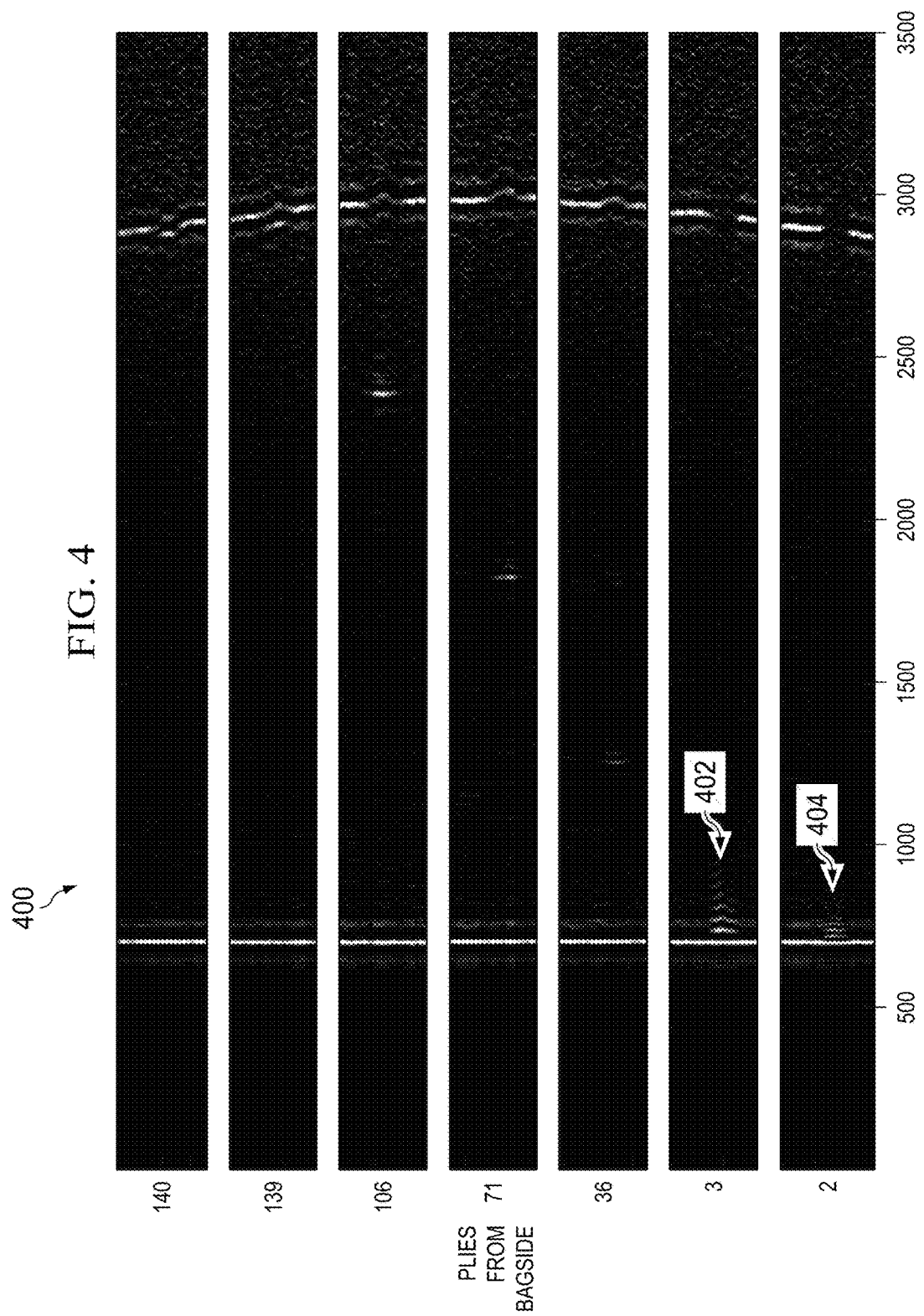
FIG. 4 is an illustration of a bandpass filtered B-scan in accordance with an illustrative embodiment.

Turning now to FIG. 4, an illustration of a bandpass filtered B-scan is depicted in accordance with an illustrative embodiment. Images 400 are graphical depictions of plurality of A-scans 300 of FIG. 3.

Images 400 are formed from data having a 2-7 MHz bandpass filter. Using this 2-7 MHz bandpass filter allows for measurements of echo 402 and echo 404. Echo 402 is indicative of a near surface inconsistency. Echo 404 is indicative of a near surface inconsistency. However, using images 400, depths of the near surface inconsistencies are not determined.

Figure 5:
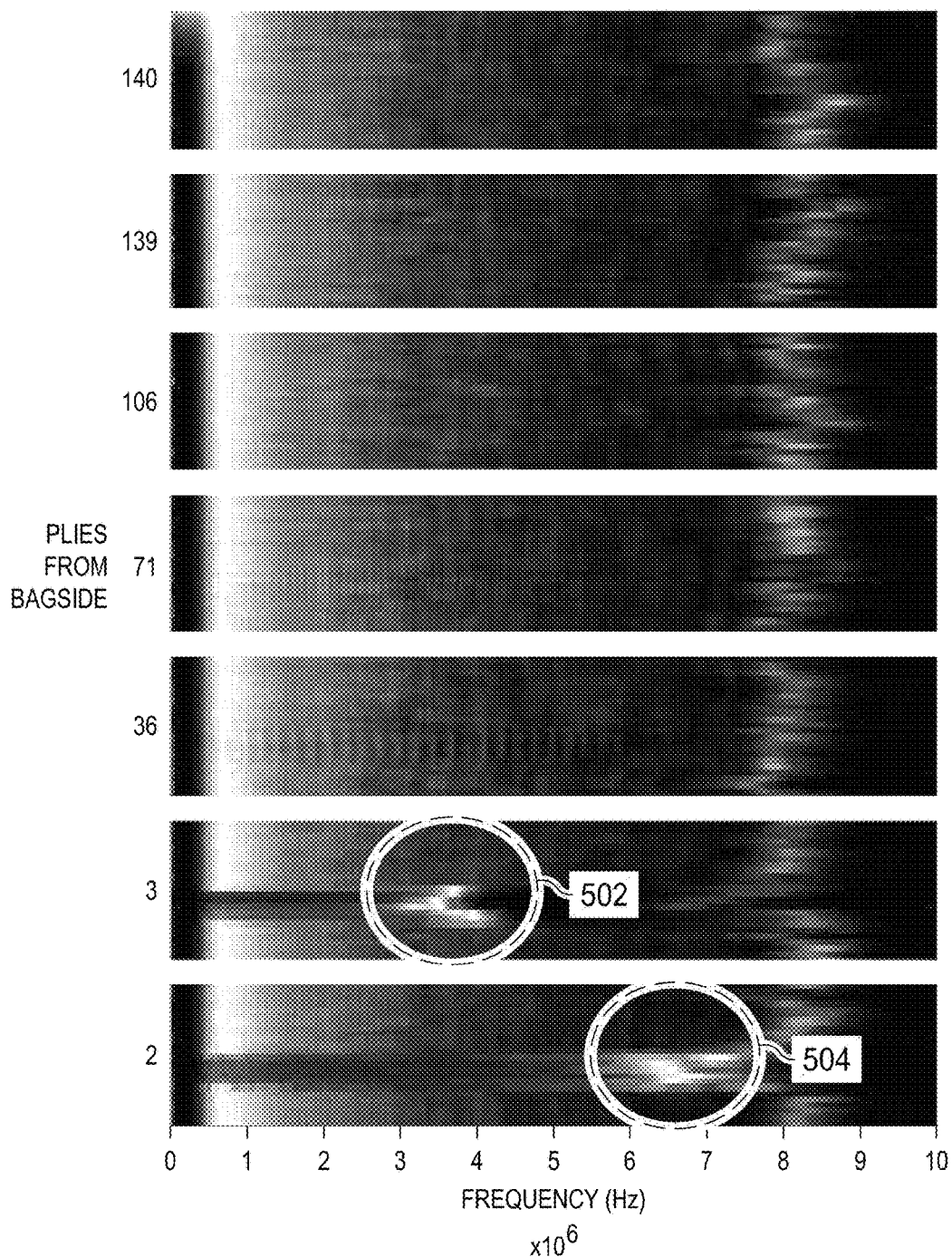
FIG. 5 is an illustration of a series of normalized frequency power images in accordance with an illustrative embodiment.

Turning now to FIG. 5, an illustration of a series of normalized frequency power images is depicted in accordance with an illustrative embodiment. Plurality of B-scans 500 is a plurality of B-scans of the Fast Fourier Transformed data for the data shown in images 400 of FIG. 4. Frequency 502 and frequency 504 are indicative of near surface defects. By identifying values for frequency 502 and frequency 504, depths of the respective near surface inconsistencies are identified.

Frequency 502 and frequency 504 are shifted from the interply frequency of the composite structure. The composite structure of FIGS. 3-5 is 0.98 inches thick and has 142 plies. Thus, each ply is 0.98/142 inches or 0.0069 inches thick. The interply frequency for composite structure is $1/((0.0069*2)/0.1181$ inches/µs) wherein 0.1181 inches/µs is the speed of sound through the composite structure. The interply frequency is 8.55 MHz. The interply frequency is shown at location 506 in each B-scan of plurality of B-scans 500.

In some other examples, data may be displayed for a metallic substrate rather than a composite material. Metals do not have an interply frequency. Accordingly, when the structure has a metal substrate, location 506 will not have an interplay frequency.

As depicted, frequency 502 is 3.915 MHz. The depth of the near surface inconsistency in the composite structure is determined using the equation (1/3.915 MHz)*(0.1181 in/µs/2). The depth of the near surface inconsistency is 0.0151 inches. Using the ply thickness of 0.0069 inches, the depth of the near surface inconsistency is determined to be 0.0151 inches/0.0069 inches which is greater than two plies, but less than three plies from the surface of the composite structure.

As depicted, frequency 504 is 6.763 MHz. The depth of the near surface inconsistency in the composite structure is determined using the equation (1/6.763 MHz)*(0.1181 in/µs/2). The depth of the near surface inconsistency is 0.0087 inches. Using the ply thickness of 0.0069 inches, the depth of the near surface inconsistency is determined to be 0.0087 inches/0.0069 inches which is greater than one ply, but less than two plies from the surface of the composite structure.

Plurality of B-scans 500 is data for a specific composite structure presented only for demonstration of the illustrative embodiments. The data and calculations presented are only presented as non-limiting examples as to how near surface inconsistencies are identified. The characteristics presented such as the depths of inconsistencies, thickness of the composite structure, thickness of plies, quantity of plies, or any other characteristics are not limiting.

Figure 6:
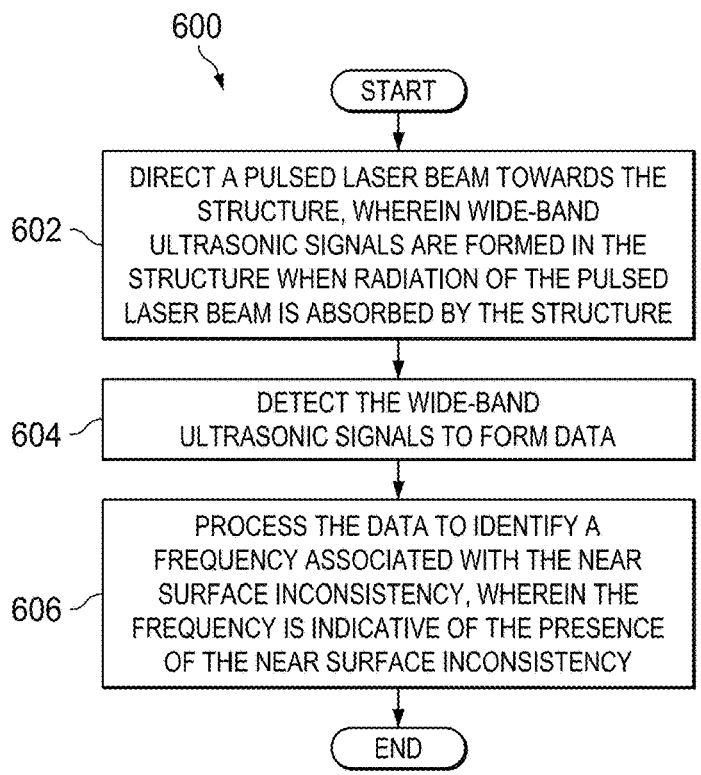
FIG. 6 is an illustration of a flowchart of a process for detecting a presence of a near surface inconsistency in a structure in accordance with an illustrative embodiment.

Turning now to FIG. 6, an illustration of a flowchart of a process for detecting a presence of a near surface inconsistency in a structure is depicted in accordance with an illustrative embodiment. Process 600 is performed in inspection environment 200 using laser ultrasound inspection system 204 and processor 226 of FIG. 2. Process 600 detects near surface inconsistency 230 of FIG. 2. FIGS. 3-5 depict output that may be generated during process 600. Process 600 is used to detect near surface inconsistencies in structures of aircraft 100 of FIG. 1.

Process 600 detects a near surface inconsistency in a structure. In some illustrative examples, the structure is a composite structure. In other illustrative examples, the structure is a substrate having a surface organic coating. Process 600 directs a pulsed laser beam towards the structure, wherein wide-band ultrasonic signals are formed in the structure when radiation of the pulsed laser beam is absorbed by the structure (operation 602).

Process 600 detects the wide-band ultrasonic signals to form data (operation 604). In some examples, the data comprises a number of ultrasonic A-scans in the time domain.

Process 600 processes the data to identify a frequency associated with the near surface inconsistency, wherein the frequency is indicative of the presence of the near surface inconsistency (operation 606). Afterwards the process terminates. In some illustrative examples, processing the data comprises applying a bandpass filter to the data. In some illustrative examples, the filter is a bandpass 2-10 MHz filter.

In some examples, the data comprises a number of ultrasonic A-scans, and processing the data further comprises transforming the number of ultrasonic A-scans to generate frequency domain data. Applying the filter is performed on the frequency domain data.

Figure 7:
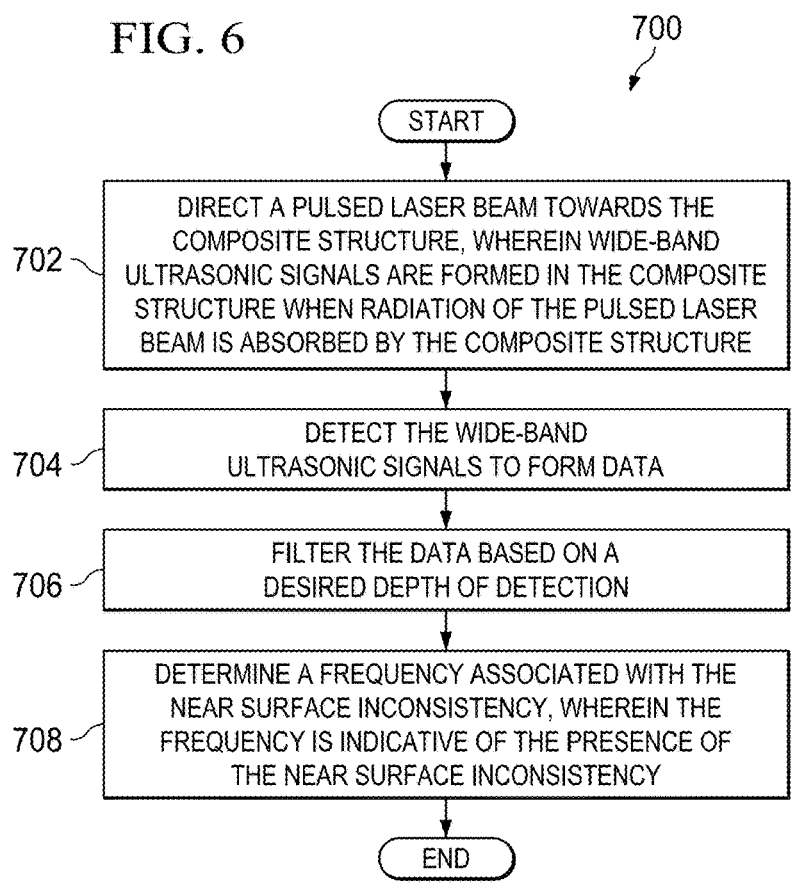
FIG. 7 is an illustration of a flowchart of a process for detecting a presence of a near surface inconsistency in a composite structure in accordance with an illustrative embodiment.

Turning now to FIG. 7, an illustration of a flowchart of a process for detecting a presence of a near surface inconsistency in a composite structure is depicted in accordance with an illustrative embodiment. Process 700 is performed in inspection environment 200 using laser ultrasound inspection system 204 and processor 226 of FIG. 2. Process 700 detects near surface inconsistency 230 of FIG. 2. FIGS. 3-5 depict output that may be generated during process 700. Process 700 is used to detect near surface inconsistencies in composite structures of aircraft 100 of FIG. 1.

Process 700 detects a near surface inconsistency in a composite structure. Process 700 directs a pulsed laser beam towards the composite structure, wherein wide-band ultrasonic signals are formed in the composite structure when radiation of the pulsed laser beam is absorbed by the composite structure (operation 702). Process 700 detects the wide-band ultrasonic signals to form data (operation 704). In some illustrative examples, the data comprises a number of ultrasonic A-scans.

Process 700 filters the data based on a desired depth of detection (operation 706). In some illustrative examples, filtering the data comprises applying a bandpass filter to the data. In some illustrative examples, the filter is a bandpass 2-10 MHz filter.

Process 700 determines a frequency associated with the near surface inconsistency, wherein the frequency is indicative of the presence of the near surface inconsistency (operation 708). Afterwards the process terminates.

Figure 8:
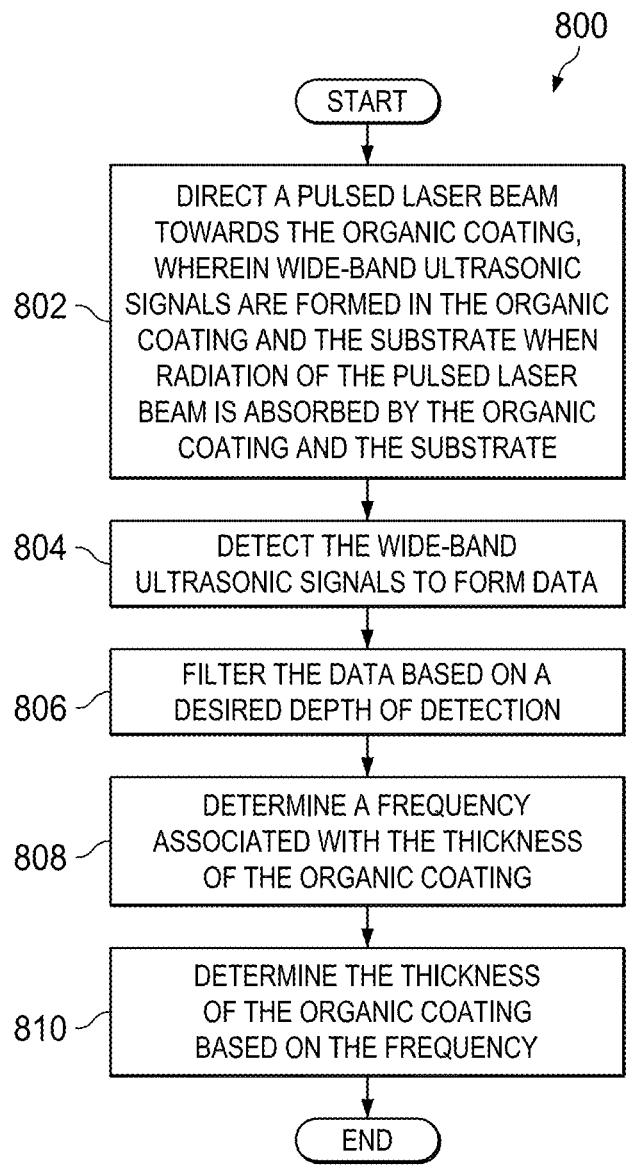
FIG. 8 is an illustration of a flowchart of a process for measuring thickness of an organic coating on a surface of a substrate in accordance with an illustrative embodiment.

Turning now to FIG. 8, an illustration of a flowchart of a process for measuring thickness of an organic coating on a surface of a substrate is depicted in accordance with an illustrative embodiment. Process 800 is performed in inspection environment 200 using laser ultrasound inspection system 204 and processor 226 of FIG. 2. Process 800 detects near surface inconsistency 230 of FIG. 2. Process 800 is used to detect near surface inconsistencies of an organic coating on a surface of a substrate forming a component of aircraft 100 of FIG. 1.

Process 800 measures thickness of an organic coating on a surface of a substrate. Process 800 directs a pulsed laser beam towards the organic coating, wherein wide-band ultrasonic signals are formed in the organic coating and the substrate when radiation of the pulsed laser beam is absorbed by the organic coating and the substrate (operation 802).

Process 800 detects the wide-band ultrasonic signals to form data (operation 804). Process 800 filters the data based on a desired depth of detection (operation 806). In some illustrative examples, filtering the data comprises applying a bandpass filter to the data. In some illustrative examples, the bandpass filter is a bandpass 2-10 MHz filter.

Process 800 determines a frequency associated with the thickness of the organic coating (operation 808). Process 800 determines the thickness of the organic coating based on the frequency (operation 810). Afterwards the process terminates.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

In one example, process 600 further comprises determining a depth of the near surface inconsistency using the frequency. In some examples, determining the depth of the near surface inconsistency comprises using the equation $(1/f)*s/2=d$, wherein f is the frequency, wherein s is the speed of sound through the structure, and wherein d is the depth of the near surface inconsistency. In some examples, the structure is a composite structure and the method further comprises determining a location of the near surface inconsistency based on the depth and ply thickness data of the structure.

In other illustrative examples, the structure is a substrate having a surface organic coating, and the near surface inconsistency is a difference in thickness of the surface organic coating. In these examples, the method further comprises determining a thickness of the near surface inconsistency using the frequency. In some examples, determining the thickness of the near surface inconsistency comprises: using the equation $(1/f)*s/2=d$, wherein f is the frequency, wherein s is the speed of sound through the surface organic coating, and wherein d is the thickness of the near surface inconsistency.

In some illustrative examples, the data comprises a number of ultrasonic A-scans and process 700 further comprises transforming the number of ultrasonic A-scans to generate frequency domain data, and wherein applying the filter is performed on the frequency domain data. In some illustrative examples, process 700 further comprises determining a depth of the near surface inconsistency using the frequency and the equation $(1/f)*s/2=d$, wherein f is the frequency, wherein s is the speed of sound through the composite structure, and wherein d is the depth of the near surface inconsistency.

In some illustrative examples, the data comprises a number of ultrasonic A-scans and process 800 further comprises transforming the number of ultrasonic A-scans to generate frequency domain data, and wherein applying the filter is performed on the frequency domain data. In some illustrative examples, process 800 determining the thickness of the organic coating based on the frequency includes determining the thickness of the organic coating using the frequency and equation $(1/f)*s/2=t$, wherein f is the frequency, wherein s is speed of sound through the organic coating, and wherein t is the thickness of the organic coating.

Figure 9:
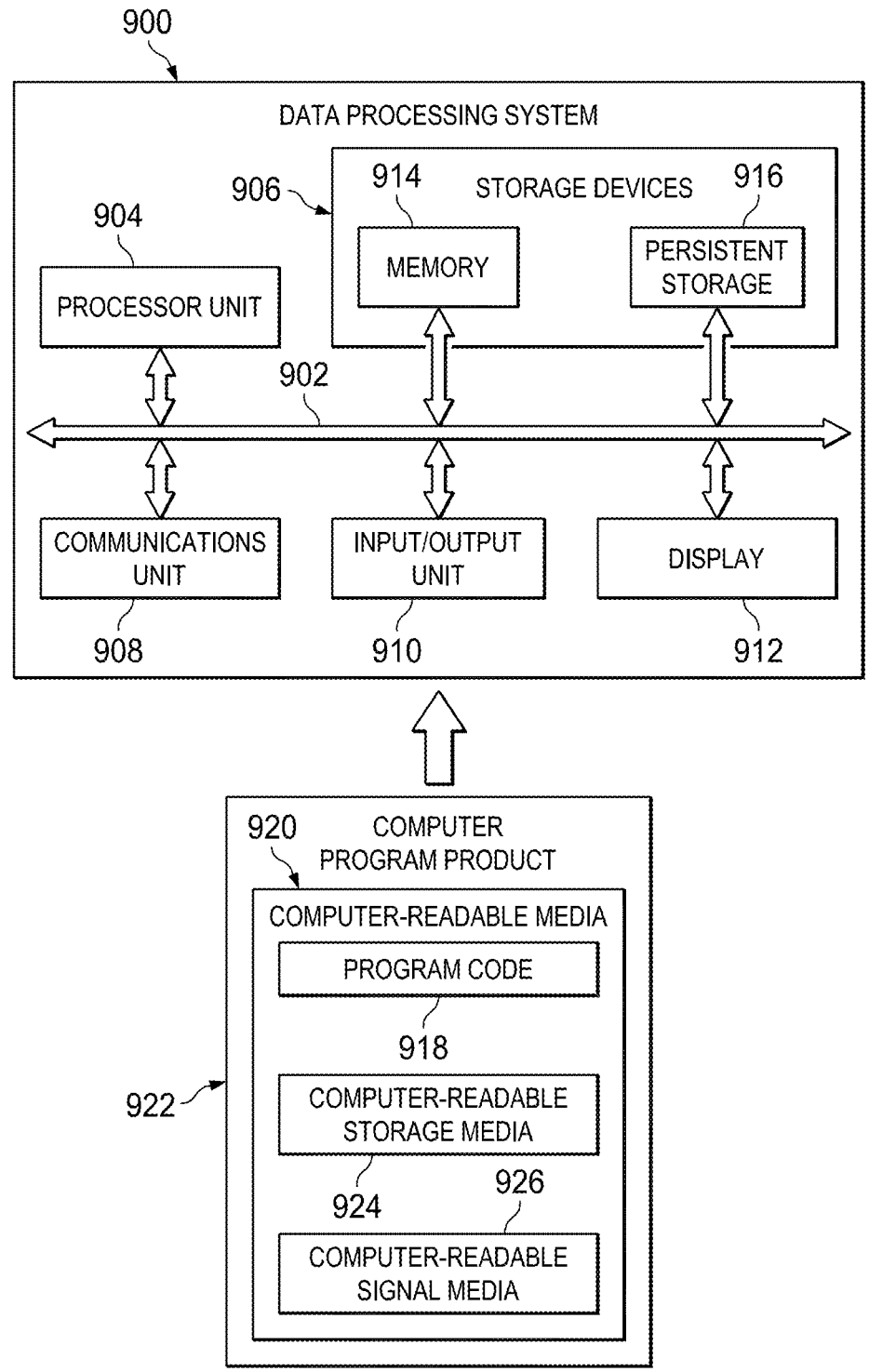
FIG. 9 is an illustration of a data processing system in the form of a block diagram in accordance with an illustrative embodiment.

Turning now to FIG. 9, an illustration of a data processing system in the form of a block diagram is depicted in accordance with an illustrative embodiment. Data processing system 900 may be used to implement processor 226 of FIG. 2. Data processing system 900 may be used to process data as described in FIGS. 6-8 and display output as depicted in FIGS. 3-5. As depicted, data processing system 900 includes communications framework 902, which provides communications between processor unit 904, storage devices 906, communications unit 908, input/output unit 910, and display 912. In some cases, communications framework 902 may be implemented as a bus system.

Processor unit 904 is configured to execute instructions for software to perform a number of operations. Processor unit 904 may comprise a number of processors, a multi-processor core, and/or some other type of processor, depending on the implementation. In some cases, processor unit 904 may take the form of a hardware unit, such as a circuit system, an application specific integrated circuit (ASIC), a programmable logic device, or some other suitable type of hardware unit.

Instructions for the operating system, applications, and/or programs run by processor unit 904 may be located in storage devices 906. Storage devices 906 may be in communication with processor unit 904 through communications framework 902. As used herein, a storage device, also referred to as a computer readable storage device, is any piece of hardware capable of storing information on a temporary and/or permanent basis. This information may include, but is not limited to, data, program code, and/or other information.

Memory 914 and persistent storage 916 are examples of storage devices 906. Memory 914 may take the form of, for example, a random access memory or some type of volatile or non-volatile storage device. Persistent storage 916 may comprise any number of components or devices. For example, persistent storage 916 may comprise a hard drive, a flash memory, a rewritable optical disk, a rewritable magnetic tape, or some combination of the above. The media used by persistent storage 916 may or may not be removable.

Communications unit 908 allows data processing system 900 to communicate with other data processing systems and/or devices. Communications unit 908 may provide communications using physical and/or wireless communications links.

Input/output unit 910 allows input to be received from and output to be sent to other devices connected to data processing system 900. For example, input/output unit 910 may allow user input to be received through a keyboard, a mouse, and/or some other type of input device. As another example, input/output unit 910 may allow output to be sent to a printer connected to data processing system 900.

Display 912 is configured to display information to a user. Display 912 may comprise, for example, without limitation, a monitor, a touch screen, a laser display, a holographic display, a virtual display device, and/or some other type of display device.

In this illustrative example, the processes of the different illustrative embodiments may be performed by processor unit 904 using computer-implemented instructions. These instructions may be referred to as program code, computer usable program code, or computer readable program code, and may be read and executed by one or more processors in processor unit 904.

In these examples, program code 918 is located in a functional form on computer readable media 920, which is selectively removable, and may be loaded onto or transferred to data processing system 900 for execution by processor unit 904. Program code 918 and computer readable media 920 together form computer program product 922. In this illustrative example, computer readable media 920 may be computer readable storage media 924 or computer readable signal media 926.

Computer readable storage media 924 is a physical or tangible storage device used to store program code 918 rather than a medium that propagates or transmits program code 918. Computer readable storage media 924 may be, for example, without limitation, an optical or magnetic disk or a persistent storage device that is connected to data processing system 900.

Alternatively, program code 918 may be transferred to data processing system 900 using computer readable signal media 926. Computer readable signal media 926 may be, for example, a propagated data signal containing program code 918. This data signal may be an electromagnetic signal, an optical signal, and/or some other type of signal that can be transmitted over physical and/or wireless communications links.

The illustration of data processing system 900 in FIG. 9 is not meant to provide architectural limitations to the manner in which the illustrative embodiments may be implemented. The different illustrative embodiments may be implemented in a data processing system that includes components in addition to or in place of those illustrated for data processing system 900. Further, components shown in FIG. 9 may be varied from the illustrative examples shown.

Figure 10:
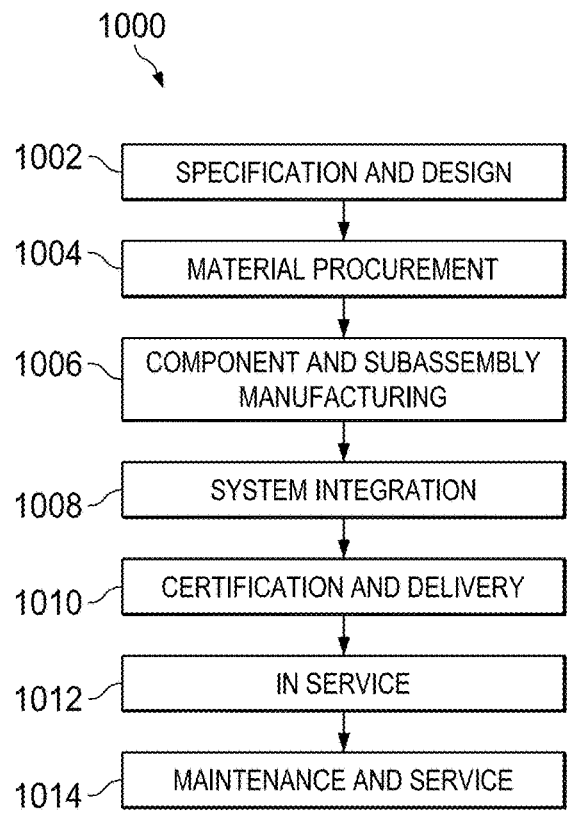
FIG. 10 is an illustration of an aircraft manufacturing and service method in the form of a block diagram in accordance with an illustrative embodiment.
Figure 11:
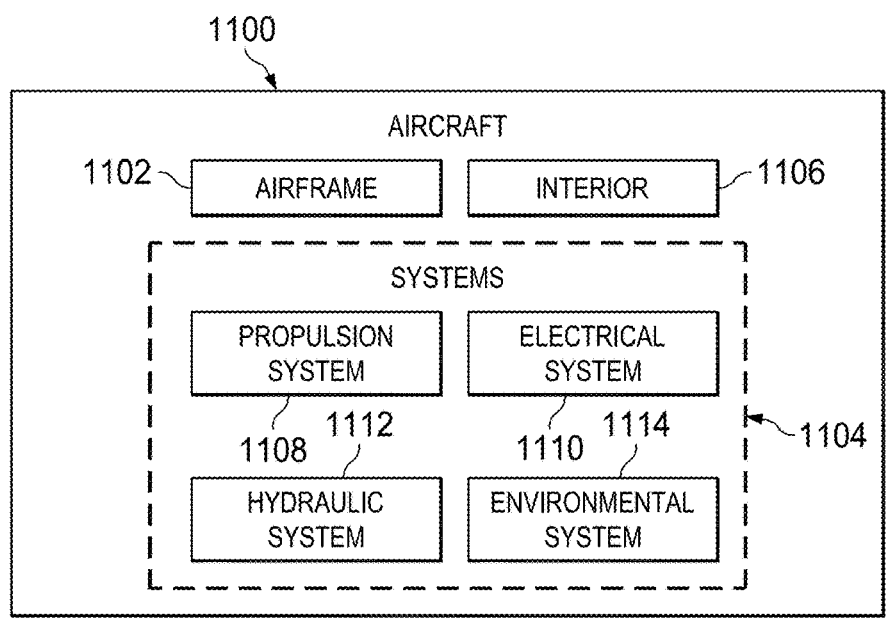
FIG. 11 is an illustration of an aircraft in the form of a block diagram in which an illustrative embodiment may be implemented.

Illustrative embodiments of the disclosure may be described in the context of aircraft manufacturing and service method 1000, as shown in FIG. 10, and aircraft 1100, as shown in FIG. 11. Turning first to FIG. 10, an illustration of an aircraft manufacturing and service method is depicted in accordance with an illustrative embodiment. During preproduction, aircraft manufacturing and service method 1000 may include specification and design 1002 of aircraft 1100 and material procurement 1004.

During production, component and subassembly manufacturing 1006 and system integration 1008 of aircraft 1100 take place. Thereafter, aircraft 1100 may go through certification and delivery 1010 in order to be placed in service 1012. While in service 1012 by a customer, aircraft 1100 is scheduled for routine maintenance and service 1014, which may include modification, reconfiguration, refurbishment, and other maintenance or service.

Each of the processes of aircraft manufacturing and service method 1000 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of an aircraft is depicted in which an illustrative embodiment may be implemented. In this example, aircraft 1100 is produced by aircraft manufacturing and service method 1000 in FIG. 10, and may include airframe 1102 with plurality of systems 1104 and interior 1106. Examples of plurality of systems 1104 include one or more of propulsion system 1108, electrical system 1110, hydraulic system 1112, and environmental system 1114. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1000 in FIG. 10. One or more illustrative embodiments may be used during component and subassembly manufacturing 1006 in FIG. 10. For example, laser ultrasound inspection system 204 in FIG. 2 may be used to inspect structures during component and subassembly manufacturing 1006. Further, laser ultrasound inspection system 204 in FIG. 2 may be used to inspect an assembly during maintenance and service 1014 in FIG. 10. For example, structures of aircraft 1100 may be inspected during scheduled maintenance for aircraft 1100 using laser ultrasound inspection system 204.

The illustrative embodiments provide a method and apparatus for detecting near surface inconsistencies. It is undesirably difficult to detect surface inconsistencies with conventional ultrasonic inspection techniques.

The illustrative embodiments present a method for finding near surface inconsistencies in a composite part by transforming time domain ultrasound data generated with laser-based ultrasound hardware into the frequency domain and then analyzing using knowledge of the material characteristics (including ply thickness) to locate inconsistencies such as delaminations. The same approach is used to accurately measure coating thickness on a composite or metallic substrate.

The illustrative embodiments allow for exploitation of broad band data received from laser-based ultrasonics to get adequate resolution for detection of near surface inconsistencies. By filtering to only look at near surface phenomena, there is enough information to find inconsistencies that cannot be found with conventional ultrasonics.

Further, laser-based ultrasonics is used to determine coating thickness measurement. Some of the coatings are applied to composite substrates. Conventional ultrasonics are not able to accurately determine coating thickness. Accurate coating thickness measurements are important to aerospace both for weight and lightning strike protection.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method of detecting a presence of a near surface inconsistency in a composite structure, the method comprising:
   directing a pulsed laser beam towards the composite structure, wherein wide-band ultrasonic signals are formed in the composite structure when radiation of the pulsed laser beam is absorbed by the composite structure;
   detecting the wide-band ultrasonic signals to form data; and
   processing the data to identify a frequency associated with the near surface inconsistency, wherein the frequency is indicative of the presence of the near surface inconsistency, wherein processing the data comprises applying a bandpass filter to the data, and wherein the bandpass filter is selected based on an interply frequency of composite material of the composite structure.

2. The method of claim 1, wherein the bandpass filter is a bandpass 2-10 MHz filter.

3. The method of claim 1, wherein the data comprises a number of ultrasonic A-scans in a time domain, wherein processing the data further comprises transforming the number of ultrasonic A-scans to generate frequency domain data, and wherein applying the bandpass filter is performed on the frequency domain data.

4. The method of claim 1 further comprising:
   determining a depth of the near surface inconsistency using the frequency.

5. The method of claim 4, wherein determining the depth of the near surface inconsistency comprises:
   using equation $(1/f)*s/2=d$, wherein f is the frequency, wherein s is speed of sound through the composite structure, and wherein d is the depth of the near surface inconsistency.

6. The method of claim 4, wherein the method further comprises:
   determining a location of the near surface inconsistency within a thickness of the composite structure based on the depth and ply thickness data of the composite structure.

7. The method of claim 1, wherein the composite structure is a substrate having a surface organic coating, and wherein the near surface inconsistency is a difference in thickness of the surface organic coating, the method further comprising:
   determining a thickness of the near surface inconsistency using the frequency.

8. The method of claim 7, wherein determining the thickness of the near surface inconsistency comprises:
   using equation $(1/f)*s/2=d$, wherein f is the frequency, wherein s is speed of sound through the surface organic coating, and wherein d is the thickness of the near surface inconsistency.

9. The method of claim 1, wherein the wide-band ultrasonic signals have a frequency in the range of 20 kilohertz to about 100 megahertz.

10. The method of claim 1, wherein the bandpass filter has a bandwidth between an upper cutoff frequency and a lower cutoff frequency of the bandpass filter of at least 5 MHz.

11. The method of claim 1 further comprising:
    determining the interply frequency of the composite structure using the equation $1/(t*2/s)=i$, wherein the t is a thickness per ply of the composite material, wherein s is the speed of sound through the composite structure, and wherein i is the interply frequency.

12. A method of detecting a presence of a near surface inconsistency in a composite structure, the method comprising:
    directing a pulsed laser beam towards the composite structure, wherein wide-band ultrasonic signals are formed in the composite structure when radiation of the pulsed laser beam is absorbed by the composite structure;
    detecting the wide-band ultrasonic signals to form data;
    filtering the data, wherein filtering the data comprises applying a bandpass filter to the data, and wherein the bandpass filter is selected based on an interply frequency of composite material of the composite structure; and
    determining a frequency associated with the near surface inconsistency, wherein the frequency is indicative of the presence of the near surface inconsistency.

13. The method of claim 12, wherein the bandpass filter is a bandpass 2-10 MHz filter.

14. The method of claim 12, wherein the data comprises a number of ultrasonic A-scans, the method further comprising:
    transforming the number of ultrasonic A-scans to generate frequency domain data, and wherein applying the bandpass filter is performed on the frequency domain data.

15. The method of claim 12 further comprising:
    determining a depth of the near surface inconsistency using the frequency and equation $(1/f)*s/2=d$, wherein f is the frequency, wherein s is speed of sound through the composite structure, and wherein d is the depth of the near surface inconsistency.

16. The method of claim 12, wherein the lower cutoff frequency of the bandpass filter is 2 MHz.

17. The method of claim 12, wherein a desired depth of detection is less than a thickness of the composite structure.

18. The method of claim 12, wherein the bandpass filter has a bandwidth between an upper cutoff frequency and a lower cutoff frequency of the bandpass filter of at least 5 MHz.

19. The method of claim 12, wherein the wide-band ultrasonic signals have a frequency in the range of 20 kilohertz to about 100 megahertz.

20. The method of claim 12 further comprising:
    determining the interply frequency of the composite structure using the equation $1/(t*2/s)=i$, wherein t is a thickness per ply of composite material, wherein s is the speed of sound through the composite structure, and wherein i is the interply frequency.

* * * * *